US005529736A

United States Patent [19]
Shalaby et al.

[11] Patent Number: 5,529,736
[45] Date of Patent: Jun. 25, 1996

[54] PROCESS OF MAKING A BONE HEALING DEVICE

[75] Inventors: Shalaby W. Shalaby, Anderson; Russell A. Johnson, Seneca; Meng Deng, Pendleton, all of S.C.

[73] Assignee: Clemson University, Clemson, S.C.

[21] Appl. No.: 288,343

[22] Filed: Aug. 10, 1994

[51] Int. Cl.⁶ .......................... B29C 43/02; B29C 43/36
[52] U.S. Cl. .................... 264/162.000; 264/322; 264/323; 264/348
[58] Field of Search .................. 264/162, 322, 264/323, 348

[56] References Cited

U.S. PATENT DOCUMENTS

| | | |
|---|---|---|
| Re. 33,348 | 9/1990 | Lower . |
| 4,175,555 | 11/1979 | Herbert . |
| 4,338,926 | 7/1982 | Kummer et al. . |
| 4,463,753 | 8/1984 | Gustilo . |
| 4,539,981 | 9/1985 | Tunc . |
| 4,550,449 | 11/1985 | Tunc . |
| 4,723,541 | 2/1988 | Reese . |
| 4,756,307 | 7/1988 | Crowninshield . |
| 4,776,329 | 10/1988 | Treharne . |
| 4,858,601 | 8/1989 | Glisson . |
| 4,858,603 | 8/1989 | Clemow et al. . |
| 5,030,402 | 7/1991 | Zachariades . |
| 5,062,843 | 11/1991 | Mahony, III . |

OTHER PUBLICATIONS

State-of-the Art in Absorbable Polymers in Hard Tissue Repair, by D. C. Tunc, *Polymer Prepr. 27(1)*, pp. 431–432, 1986.
Development of Absorbable, Ultra High Strength Polylactide, by D. C. Tunc, et al., Johnson & Johnson Products, Inc., pp. 383–387.
A High Strength Absorbable Polymer for Internal Bone Fixation, by D. C. Tunc, 9th Annual Meeting of the Society for Biomaterials, Birmingham, Ala, p. 47, 1983.
Management of the Fractured Scaphoid Using a New Bone Screw, by Timothy J. Herbert and William E. Fisher, *The Journal of Bone and Joint Surgery*, pp. 114–123, 1984.
Mechanical Properties of Biodegradable Polymers and Composites Proposed for Internal Fixation of Bone, by A. U. Daniels, et al., Journal of Applied Biomat., 1, 57, 1990.
A Review of Recent Developments in the Processing and Properties of Oriented Polyethylene, *Plastics, Rubber and Composites Processing an Applications*, vol. 19, No. 1, pp. 7–13, 1993.
Mechanical Properties of Ultra-Oriented Polyethylene, by Norman E. Weeks and Roger S. Porter, *Journal of Polymer Science: Polymer Physics Edition*, vol. 12, pp. 635–643, 1974.
Hydrostatic Extrusion of Linear Polyethylene, *Journal of Materials Science*, 9 (1974) Letters, pp. 1193–1196.

*Primary Examiner*—Leo B. Tentoni
*Attorney, Agent, or Firm*—Dority & Manning

[57] ABSTRACT

The present invention is directed to polymeric bone fixation devices and processes for making the devices. In making the bone fixation devices, a polymeric material having a crystalline portion is deformed by a compressive force along a particular direction which causes molecular chains contained within the polymer to orient. The resulting polymer has increased mechanical properties including increased tensile strength and modulus. The polymeric material used to make the bone fixation device can be a bioabsorbable polymer which, once implanted, is broken down and absorbed by the patient's body, eliminating the need for removal.

20 Claims, 4 Drawing Sheets

PROCESS OF MAKING A BONE HEALING DEVICE

BACKGROUND OF THE INVENTION

The present invention relates generally to a process for increasing the strength of polymers and articles produced thereby. In particular, the present invention is directed to bone healing devices made from higher strength bioabsorbable polymeric materials.

Traditionally, certain types of bone fractures have required the use of particular bone fixation devices or supporting members in order to promote proper healing of the bone. As used herein, a bone fixation device is any device used to heal bones and allied tissues such as cartilage, ligaments, etc. Such bone healing devices include plates, bone screws, wires, pins, staples, table ties, clips and the like. Generally, the devices are used in order to bring and maintain the fractured surfaces of a bone into close contact by applying a compressive force to the bone. Compression must be applied to the bone until there is sufficient healing for the bone to support normal loads.

One particular bone fixation device that has been found to be very useful in healing bone fractures is the Herbert bone screw which is disclosed in U.S. Pat. No. 4,175,555. The Herbert bone screw is a screw that includes a shaft having threaded portions at each end. Although like-handed, the pitch of the threaded portion at the leading end of the shaft is slightly greater than the pitch of the threaded portion at the trailing end of the shaft. When used to heal a bone fracture, this differential pitch causes the leading edge of the screw to advance axially into the remote fragment to a slightly greater extent than it does relative to the near fragments. This action puts the screw in tension and hence the fracture faces of the bone under compression. Further, the Herbert screw does not include a screw head, thus allowing the entire screw to be embedded within the bone without any protrusions.

The Herbert differential pitch bone screw has been used successfully in many different types of bone fractures and has gained growing acceptance by the medical industry. Specifically, the Herbert screw is recommended for use in fractures of the basal joint of the thumb, fractures of the head of the radius, treatment of delayed and non-union scaphoid fractures or their malunion, treatment of trans-scaphoid perilunate dislocation, internal fixation of capitellar fractures, and treatment of osteochondral fractures at various cites in the body. It is used as an alternative to wires, pins or small conventional screws.

Herbert bone screws, similar to other conventional bone fixation devices, are typically made from metals such as stainless steel or titanium alloys. However, although metal bone devices have achieved relatively high degrees of success in repairing bone fractures, these devices have some undesirable features. For instance, these metallic devices must be removed after the bone fracture has healed but before bone resorption, loosening, corrosion or infection. Removing the devices requires a second surgical procedure resulting in additional trauma to the patient as well as increased medical costs.

Another disadvantage to using bone fixation devices made from metallic substances is that the metal typically has a high modulus, is stiff and is mechanically incompatible with the bone. Use of such devices with high stiffness has been identified as a cause of stress shielding. Basically, when stress shielding occurs, the bone fixation device absorbs most of the stress applied to the bone and insulates the surrounding bone from normal loading. Stress shielding can be the cause of significant bone resorption, with consequent reduction in the strength of the bone in the region of the healed fracture. The bone thus becomes susceptible to refracture after the device is removed.

Bone fixation devices made from metals can also cause other problems including the generation of toxic metallic ions and the potential for infection. Consequently, a need exists for a bone fixation device not made from a metallic substance or alloy and which does not have to be removed from the bone. One possible solution or alternative to metallic bone healing devices is the use of polymeric materials and specifically the use of bioabsorbable polymeric materials. As used herein, a bioabsorbable material is defined as a material capable of being broken down, degraded, and ultimately absorbed by the body. For instance, bioabsorbable polymeric materials are typically degraded by the human body through a series of hydrolysis reactions which break down the polymer chains into smaller chemical units. Typically, the polymer is reduced mostly to water and carbon dioxide and absorbed into the digestive system. In the past, others have attempted to incorporate polymeric and bioabsorbable materials into bone fixation devices.

For example, U.S. Pat. Nos. 4,539,981 and 4,550,449 both to Tunc disclose a process for producing an absorbable bone fixation device. Specifically, the bone fixation device is made from a high molecular weight polylactide polymer having a low unreacted monomer content. In particular, the monomer content must be below about 2%. The process and conditions of forming the polylactide must be very carefully controlled in order to produce a polymer with sufficient strength. In fact, the reaction time in order to produce a polymer having desired characteristics is between 50 and 120 hours.

U.S. Pat. No. 4,756,307 to Crowninshield discloses a nail device to be implanted into a bone that includes a plurality of segments fastened together by a resorbable bioadhesive such that the plurality of segments are gradually disassociated after the nail device has been implanted. Specifically, the segments are joined by a "bioadhesive" such as polylactic acid, polyglycolic acid, copolymers or blends of these two, or a protein based adhesive. Once implanted, the nail device exhibits high strength characteristics and is resistent to bending and rotation. After the bioadhesive is resorbed, the plurality of segments will freely disassociate to restrict bone bending and torsion to a lesser extent than previously restricted with the solid rod. The nail device is particularly suited to fractures in the femur bone.

A resorbable compressing screw and method are disclosed in U.S. Pat. No. 4,776,329 to Treharne. In particular, Treharne is directed to hip screws in which the conventional metallic screw is replaced in whole or in part by a resorbable material. Preferably, the resorbable material is poly(DL-lactide) with a molecular weight of 40,000 to 160,000. The compression screw is formed by injection molding.

U.S. Pat. No. 4,858,603 to Clemow et al. discloses a bone pin made with a tapered polymeric portion and a cutting device secured to the smaller end of the polymeric portion. The cutting device can be used as a drill point for drilling through the bone. The polymeric portion can be made from a polymer which is absorbable in an animal body.

In U.S. Pat. No. 4,338,926 to Kummer et al., a bone prosthesis for use in healing a bone fracture is disclosed comprising a strong, rigid non-absorbable structural member and a biologically absorbable element held in use under compression against the structural member when the prosthesis is secured to the bone. After implantation, the biologically absorbable element is gradually absorbed by the body shifting stress transmission from the prosthesis to the healing bone.

A fixation screw for securing a bone graft of a tendon section emplaced in a ligament tunnel is disclosed in U.S. Pat. No. 5,062,843 to Mahony. The fixation screw can be formed from a biocompatible plastic or bioabsorbable material that is soft for preventing the threads of the screw from cutting into and damaging the bone grafts. Preferably, the material is made from ultrahigh molecular weight polyethylene.

A process for producing ultrahigh molecular weight ]polyethylene products including orthopedic prosthetic implants is disclosed in U.S. Pat. No. 5,030,402 to Zachariades. However, polyethylene is not considered a bioabsorbable polymer. The process includes compressing ultrahigh molecular weight polyethylene between a pair of molding plates to produce the shape of the final product. A perimeter access zone is included for allowing excess polymer in the mold cavity to deform past the mold cavity during its compression. The mold may be circular, rectangular or any other shape.

Other bone fixation devices are disclosed in U.S. Pat. No. 4,858,601 to Glisson which is directed to an adjustable compression bone screw; U.S. Pat. No. 4,723,541 to Reese which is directed to a bone screw and method; U.S. Pat. No. 4,463,753 to Gustilo which is directed to a compression bone screw; and U.S. Pat. No. Re. 33,348 to Lower which is directed to a bone screw.

Although the prior art shows the use of various bone fixation devices made in whole or in part from bioabsorbable materials, the prior art still has many deficiencies and drawbacks. Ideally, the materials used to make the bone fixation devices would have the initial biocompatibility, strength and ductility of stainless steel, would retain these properties for several weeks or months; and then undergo benign and complete biodegradation, absorption, and/or excretion. However, in the past such bioabsorbable materials have not exhibited enough strength or have retained enough strength for a required period of time.

All published work from 1980 to 1988 regarding mechanical properties of biodegradable polymers and composites proposed for use in internal fixation in place of stainless steel was reviewed and critiqued in an article entitled "Mechanical Properties of Biodegradable Polymers and Composites Proposed for Internal Fixation of Bone" authored by Daniels et al. In conclusion, Daniels et al. stated that completely biodegradable materials described to date do not meet all the requirements for replacing stainless steel devices including especially stiffness and ductility. In summary, the prior art devices have been only moderately successful. The bioabsorbable materials disclosed in the past have only been used in particular clinical applications using specific methods of fixation that are designed to be compatible with the physical characteristics of the material.

The present invention recognizes and addresses the above-described deficiencies and drawbacks of the prior art. In particular, the present invention is directed to a process for enhancing the physical characteristics of bioabsorbable materials and of all polymers in general. Specifically, the process of the present invention increases the mechanical properties of polymers by orienting the molecular chains contained within the material.

SUMMARY OF THE INVENTION

The present invention recognizes and addresses the foregoing disadvantages, and others of prior art constructions and methods.

Accordingly it is an object of the present invention to provide bone fixation devices made from polymeric materials.

It is another object of the present invention to provide bone fixation devices made from polymeric materials in which the polymeric materials are bioabsorbable.

It is another object of the present invention to provide a process for enhancing the mechanical characteristics of polymeric materials.

Still another object of the present invention is to provide a process for producing bone fixation devices including bone screws made from bioabsorbable materials.

Still another object of the present invention is to provide a process for orienting the molecular chains contained in bioabsorbable materials.

These and other objects of the present invention are achieved by providing a process for increasing the strength of polymeric materials used to make bone fixation devices. The process includes the steps of providing a thermoplastic polymer having at least a 3% crystalline structure. The polymer is deformed along a particular direction causing the polymer to expand substantially only in that direction. This deforming step causes molecular chains contained within the polymer to orient for increasing the strength of the polymer. The polymer can then subsequently be formed into a bone fixation device.

The process can further include the step of heating the polymer before being deformed to a temperature sufficient to soften the polymer without melting the crystalline structure. Also, the process can include the step of repeatedly deforming the polymer. For instance, the polymer can also be deformed along a second and different direction prior to forming the bone fixation device.

The polymer can be from about 3% to about 80% crystalline and preferably from about 20% to about 50%. In one embodiment, the polymer used in the process of the present invention can be a bioabsorbable polymer. Such bioabsorbable polymers include poly-alpha-hydroxy acids, polylactones, polyoxalates, and copolymers thereof. When using bioabsorbable polymers, the resulting bone fixation device has sufficient strength to support a fractured bone and, once implanted, can retain its strength for a period of time sufficient to heal the bone before being broken down by normal body processes.

In one embodiment, the polymeric material can be deformed in a mold cavity by applying a compressive force. The mold cavity can have a width generally corresponding to the width of the thermoplastic polymer for only allowing deformation in one direction. If the polymer is heated prior to being deformed, preferably the polymer is cooled under compression before being formed into a bone fixation device. Further, when applying the compressive force, an inclined surface can be used for also applying a shearing force to the polymer.

Upon being deformed, the thickness of the polymer can be reduced by about 10% to about 85%. Preferably, the ratio of initial thickness to final thickness of the polymer after the compressing step is from about 1.2 to about 6.0.

These and other objects are also achieved by providing a process for making bone fixation devices from bioabsorbable polymers with increased strength and modulus. The process includes the steps of providing a bioabsorbable polymer having an amorphous portion and a crystalline portion. The crystalline portion is at least about 3% of the polymer. The bioabsorbable polymer is heated to a temperature between the softening point and the melting point of the polymer. The polymer is then forced through a mold cavity having a decreasing diameter. In particular, the polymer is forced through the cavity in a spiral motion causing molecular chains contained within the polymer to extend in a helical orientation. This orientation results in increased longitudinal and radial strength. After being forced through the mold cavity, the polymer can then be formed into a bone fixation device.

As before, the bioabsorbable polymer chosen for this process can be a polymer selected from the group consisting of poly-alpha-hydroxy acids, polylactones, polyoxalates, and copolymers thereof. The process can also include the step of cooling the oriented polymer prior to being formed into a bone fixation device.

In another embodiment of the present invention, a bone fixation device is provided. The bone fixation device is made from a polymeric material having at least a 3% crystalline structure. The polymeric material contains molecular chains which have been oriented along a particular direction for increasing the mechanical properties of the device. Preferably, the bone fixation device is made from a bioabsorbable polymer. If the polymer is bioabsorbable, the polymeric material can have a tensile strength of approximately 10 kg/mm$^2$. In particular, the bone fixation device can be a bone screw or a bone pin. When using a bioabsorbable polymer, the device has sufficient strength to support a fractured bone and can retain sufficient strength to heal the bone once implanted.

Other objects, features and aspects of the present invention are discussed in greater detail below.

BRIEF DESCRIPTION OF THE DRAWINGS

A full and enabling disclosure of the present invention, including the best mode thereof to one of ordinary skill in the art is set forth more particularly in the remainder of the specification, including reference to the accompanying figures in which.

Repeat use of reference characters in the present specification and drawings is intended to represent same or analogous features or elements of the invention.

DETAILED DESCRIPTION OF PREFERRED EMBODIMENTS

According to the present invention, the mechanical properties of polymeric materials, and in particular bioabsorbable polymeric materials, can be enhanced for forming into various bone healing devices. In very general terms, the present invention is directed to a process which increases the strength of polymeric materials. In one embodiment, the process includes the step of unidirectionally deforming a polymeric substrate causing molecular chains and crystal structures contained within the polymer to orient and align in the direction of deformation. The resulting polymer has increased modulus and strength, especially along the direction of orientation. The polymer can then be formed as desired into one of various bone fixation devices for promoting the healing of fractured bones.

Such bone fixation devices include plates, bone screws, wires, pins, staples, table ties, clips and the like and can be used to heal bones and allied tissues. One particular bone healing device, a Herbert-type bone screw, is generally illustrated at 10 in FIG. 1. Bone screw 10 includes a shaft 12 having a first threaded portion 14 and a second threaded portion 16. As shown, although like handed, the pitch of threaded portion 14 is greater than the pitch of threaded portion 16. Also, the diameter of shaft 12 is less at portion 14 than at portion 16. When implanted within a bone, the differential pitch causes the leading edge of the screw to advance axially into the bone at a slightly greater rate than the trailing edge of the screw. This action allows screw 10 to apply a compressive force against two pieces of a fractured bone for promoting healing of same.

Figure 1:
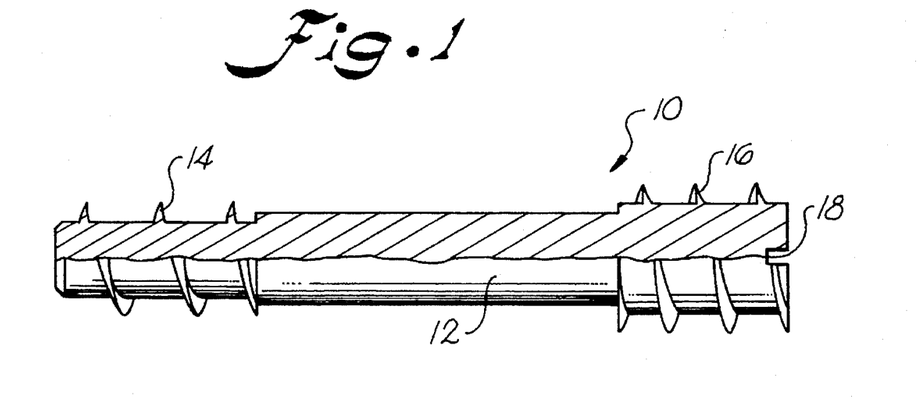
FIG. 1 is a perspective view with cut-away portions of a bone screw made according to the process of the present invention.

Bone screw 10 further includes a transverse slot 18 to which a screwdriver or other similar instrument may be applied for installing screw 10 into a bone. As shown, bone screw 10 does not include a conventional screw head, thus allowing the entire screw to be implanted within a bone.

As described above, similar bone screws have been conventionally made from metals. Although adequate, these materials possess inherent deficiencies and drawbacks. As such, the present invention is directed to using polymeric materials and in particular bioabsorbable materials to form bone screw 10 or other similar bone fixation devices as will be described hereinafter.

As briefly introduced above, the present invention includes a process for enhancing the mechanical properties of polymers by orienting molecular chains and crystal structures contained therein. In general, any thermoplastic polymer and more specifically any thermoplastic polymer that is at least about 3% crystalline can be used in the process of the present invention. A small amount of crystallinity is believed to be necessary in order to stabilize the resulting structure of the polymer. For instance, once the molecular chains contained within the amorphous portion of the polymer are oriented, the crystalline portion of the polymer is believed to maintain those chains in their extended and oriented positions. As such, once processed according to the present invention, the amorphous portion of the polymer is predominantly responsible for the enhanced strength while the crystalline portion provides a stabilizing effect.

Providing and preparing polymers having some degree of crystallinity is well known to one skilled in the art and such polymers are readily available from various suppliers and manufacturers. For instance, one method to promote the formation of crystalline structures is to heat a polymeric material, apply pressure and then cool. The polymer can then be annealed at a particular temperature for a predetermined amount of time to encourage crystalline formation and growth. For purposes of the present invention, the polymer can have a crystalline structure of from about 3% to about 80% by volume. Preferably the polymer has a crystallinity of from about 20% to about 55% and most preferably from about 25% to about 45%.

The polymeric material chosen for use in the present invention can be either a bioabsorbable polymer or a non-bioabsorbable polymer. Polymers that are not bioabsorbable would be used to make bone fixation devices or prosthetics that are to be permanently implanted within a person's body. In general, these polymers also exhibit higher strengths. Examples of non-bioabsorbable polymers that are particularly applicable for use in the present invention include polypropylene, polyethylene, such as high density polyethylene and ultra high molecular weight polyethylene, and also polyetheretherketone (PEEK).

Preferably, the present invention is directed to the use of bioabsorbable polymers for healing bone fractures and allied tissues. Ideally, once implanted the produced polymers would initially have the strength and ductility comparable to the bone being treated, would retain these properties for a sufficient period of time for the bone to heal, and then would undergo benign and complete biodegradation, absorption, and/or excretion. Bioabsorbable polymers that are believed useful in the present invention include poly-alpha-hydroxy ester acids, polylactones, polyoxalates, and copolymers thereof. Such polymers would include polylactide, polyglycolide, poly-E-caprolactone, polydioxanones, poly ortho esters, polyanhydrides, poly ester amides and copolymers thereof. Examples of poly-alpha-hydroxy ester acids would include polyhydroxyacetate, polyhydroxybutyrate, polyhydroxyvalerate, and copolymers thereof.

Preferred specific examples of bioabsorbable polymers for use in the present invention include lactide and glycolide based polymers and copolymers, P-dioxanone, and trimethylene carbonate, oxalate based polymers and copolymers.

Once an appropriate polymer is chosen or prepared, the polymer is then deformed under a compressive force in order to induce the orientation of molecular chains contained within the polymer. The polymers preferably deform in a specially designed mold which induces the polymer to flow in a unidirectional manner when a force is applied. The polymer can be first heated prior to application of the compressive force. A heating step reduces the amount of force required to induce flow. The polymer can be heated prior to being placed within the mold or can be heated by the mold itself.

If first heated, the polymer should be heated to a temperature sufficient to soften the amorphous portion of the polymer but at a temperature insufficient to melt the crystalline structure. Such a temperature is referred to as the glass transition temperature and refers to a temperature in which the amorphous portion of the polymer has more fluid-like characteristics. Preferably, the temperature is chosen from a range between the softening point and the melting point of the polymer. Of course, the actual temperature will depend upon the specific polymer being used and its corresponding physical characteristics.

Whether preheated or not, the next step in producing a polymer with enhanced physical properties is to apply a compressive force to the polymer sufficient to cause deformation. As described, preferably the polymer is placed into a mold where a pressure is applied sufficient to cause orientation and alignment of the polymer chains. The force is applied to the polymer such that deformation only occurs in one direction for maximizing chain orientation.

Figure 2:
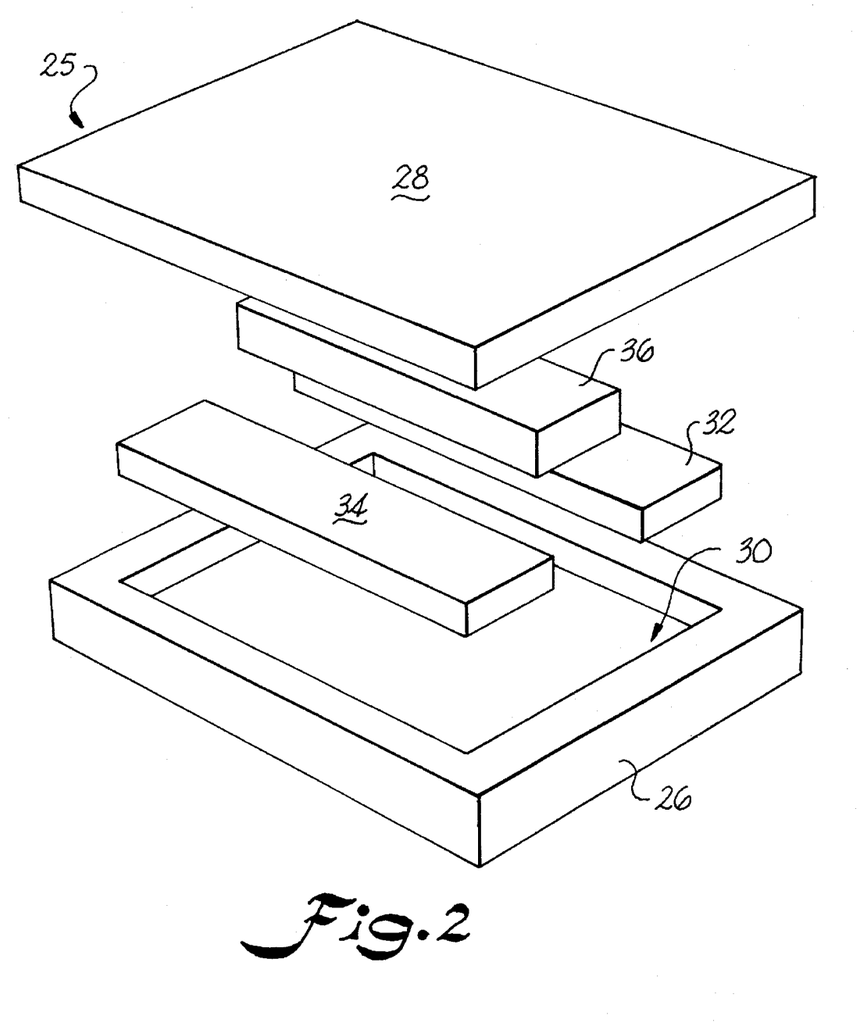
FIG. 2 is a perspective view of one embodiment of a mold that can be used in the process of the present invention.

Referring to FIG. 2, one embodiment of a mold generally illustrated at 25 is shown which can be used in the process of the present invention. Mold 25 includes a base 26 and a compression plate 28. Base 26 includes a mold cavity 30 in which the polymer is placed. In particular, the polymer can be placed within mold cavity 30 in between a pair of guide plates 32 and 34. Guide plates 32 and 34 can be sized so that when they are positioned within cavity 30, the guide plates form a channel which has approximately the same width as the polymer. In other words, guide plates 32 and 34 are placed in mold cavity 30 adjacent to the mold's opposite sides. The polymeric substrate is then placed tightly in between the two guide plates.

A compression bar 36 is also provided which approximately has the same width as the channel defined by guide plates 32 and 34. Compression bar 36 is placed on top of the polymeric substrate. Compression plate 28 is then placed upon base 26 and a compressive force is applied causing the polymer to deform and flatten in between guide plates 32 and 34.

Preferably, the polymer used within mold 25 has a length that is smaller than the length of mold cavity 30 so that there is space for the polymer to extend or flow in a lengthwise direction. During compression, the length of the polymer is increased while its thickness is decreased. The polymer can be positioned in the middle of mold cavity 30 causing the polymer to extend or flow at both ends when a force is applied or can be placed against a wall in cavity 30 only causing one end of the polymer to flow. Of importance, is that the polymer only extends in one direction, the lengthwise direction, so as to maximize polymer chain orientation.

Once placed in mold cavity 30, the polymeric substrate is deformed in amounts sufficient to increase the strength and modulus of the polymer. The actual amount of deformation will depend upon the initial size of the substrate and the strength that is needed or required in the resulting article. In general, the thickness of the polymer can be reduced by about 10% to about 85% depending upon the application. A compression ratio refers to the ratio of initial thickness to final thickness of the polymeric substrate. Here, polymers have exhibited enhanced strength and other desirable properties when the compression ratio was from about 1.2 to about 12.0. Thus far, the best results have been obtained when the compression ratio was from about 1.5 to about 5.

Once the compressive force is applied and the polymer is sufficiently deformed, the polymer can then be cooled and formed into a desired article such as a bone fixation device. Although not necessary, the polymer is preferably cooled while still under compression. Cooling under compression inhibits the oriented polymer chains from reverting back to a coiled, lower energy state position. As described above, the presence of the crystalline structure also acts to maintain the polymer chains in their oriented state. Once cooled, the position of the molecular chains become fixed within the solid block of polymer.

After cooling, the polymeric material can then be formed into any desired object. There exists a variety of different methods for producing the desired object from the polymeric substrate as one skilled in the art can appreciate. For instance, in making a bone screw, the polymer can first be cut to a desired dimension and then lathed to a rod having a predetermined diameter. The threads of the screw can then be tapped with an appropriate tool having the proper pitch. Other devices can be ground and machined as desired. When forming a fixation device, however, it is important that the polymer is not heated to its softening point. If heated, the molecular chains within the polymer may revert back to an unoriented position with coiled conformation.

Of course, besides bone screws, other bone fixation devices can be made. Such devices can include pins, plates, wires, staples, clips and the like.

In the process of the present invention, polymeric articles can be produced with increased tensile strength, modulus, and other enhanced physical characteristics. In particular, the strength of the polymer is predominantly increased in the direction of deformation and orientation. Consequently, when using articles formed by the process of the present invention, the polymeric article should be positioned so that the direction of orientation corresponds with the loads to be supported by the article.

Besides increasing strength and modulus, the process of the present invention is also believed to increase the useful life of bioabsorbable polymers. In particular, it is believed that bioabsorbable polymers produced by the present invention may not only be able to support more loads but will also retain their strength for a longer period of time once implanted into the body. In the past, some bioabsorbable polymers have not retained adequate strength to promote healing of the bone before being broken down and absorbed by normal body processes.

Figure 3:
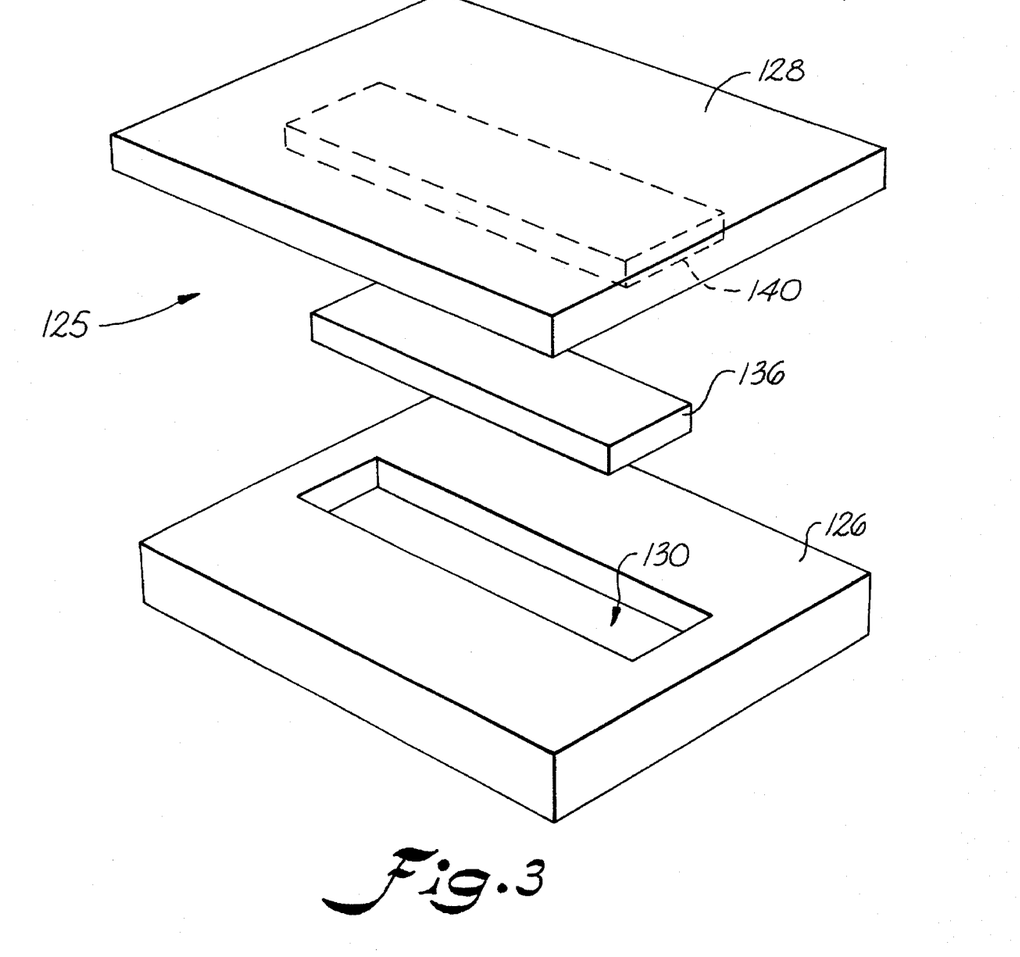
FIG. 3 is a perspective view of another embodiment of a mold that can be used in the process of the present invention.

Referring to FIG. 3, another embodiment of a mold that may be used in the process of the present invention is shown. As before, mold 125 includes a compression plate 128 and a base 126. Base 126 defines a mold cavity 130 in which a polymer substrate is placed and deformed. A compression bar 136 which has approximately the same dimensions as mold cavity 130 is placed on top of the polymer. Compression plate 128 is then brought down on top of base 126 allowing a guide tab to be placed on top of compression bar 136 and into mold cavity 130.

Mold 125 works similarly to mold 25 shown in FIG. 2. Mold cavity 130, however, is made with predetermined, fixed dimensions for mass producing oriented polymers of approximately the same size. Also, compression plate 128 includes guide tab 140 which has approximately the same dimensions as mold cavity 130. Guide tab 140 guides compression plate 128 on top of base 126 and prevents the two plates from sliding during compression.

Figure 4A:
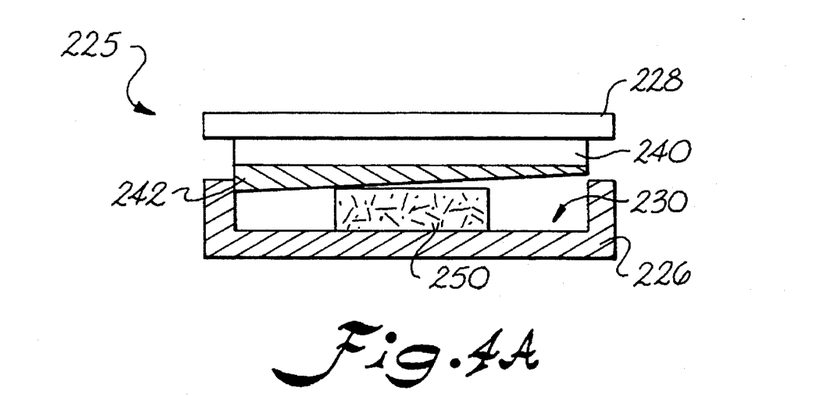
FIGS. 4A, 4B and 4C are side views of still another embodiment of a mold that can be used in the process of the present invention and, in combination, illustrate the compression of a polymeric material.
Figure 4B:
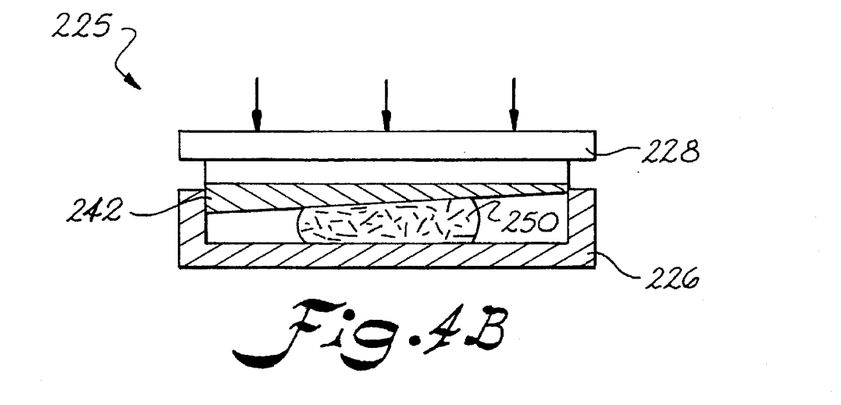
Figure 4C:
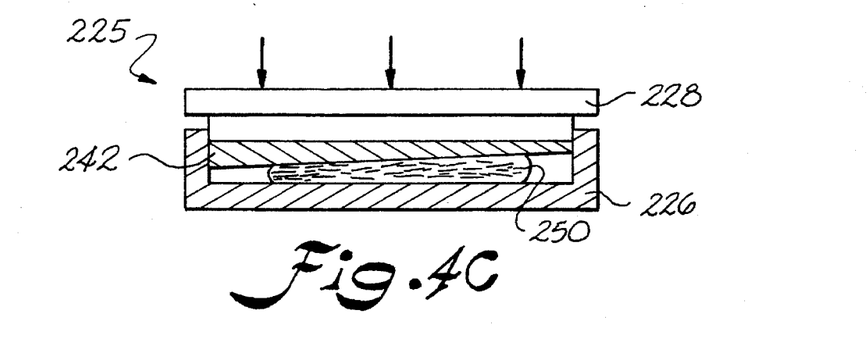

Still another embodiment of a mold that may be used in the process of the present invention is illustrated sequentially in FIGS. 4A, 4B and 4C. Referring to FIG. 4A, mold 225, similar to mold 125 in FIG. 3, includes a base 226 defining a mold cavity 230. A compression plate 228 having a guide tab 240 attached thereto is brought together with base 226.

Unlike FIGS. 2 and 3, compression plate 228 includes an inclined surface 242 for contact with a polymeric substrate 250. Inclined surface 242 when compressed against polymer 250 provides a shearing force which aids in orienting the molecular chains. FIGS. 4B and 4C illustrate the results of applying a force to ,compression plate 228 which in turn deforms and induces flow of polymer 250. In particular, polymer 250 is shown containing molecular chains and crystal structures which are oriented and aligned as specifically shown in FIG. 4C. Again, the polymer is deformed unidirectionally for orienting the polymer chains in substantially one direction. The resulting polymer has increased strength and enhanced physical properties.

As shown in FIGS. 4A, 4B and 4C, polymer 250 is shown positioned approximately in the middle of mold cavity 230. However, as described above, polymer 250 may also be positioned against a wall within the cavity for only allowing one end of the polymer to flow or extend. This method may be practical in certain applications and under certain conditions.

In an alternative process, a polymeric substrate can be placed in a mold similar to those illustrated in FIGS. 2, 3 and 4 and unidirectionally compressed and oriented as described above. If desired, the oriented substrate can then be repositioned within the mold cavity and the process can be repeated for orienting the polymer in a different direction. This method can be used to increase the strength of the polymer in multiple directions or along multiple axes. In particular, the polymer can be repositioned within the mold at any angle to the original direction of orientation.

Figure 5:
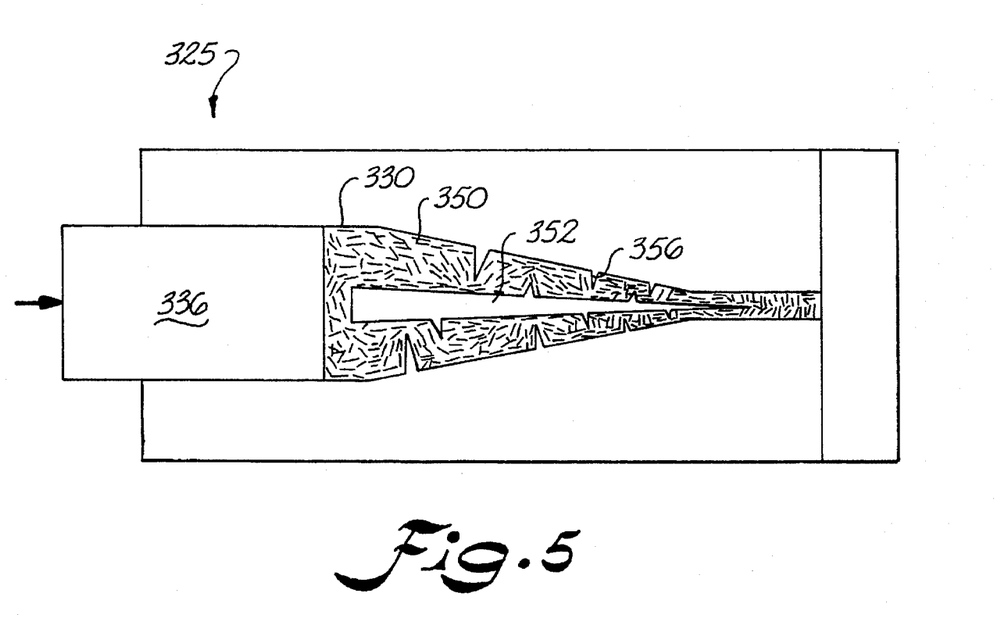
FIG. 5 is a side view of another mold that may be used in the process of the present invention and illustrates a polymeric material being compressed therein.
Figure 6:
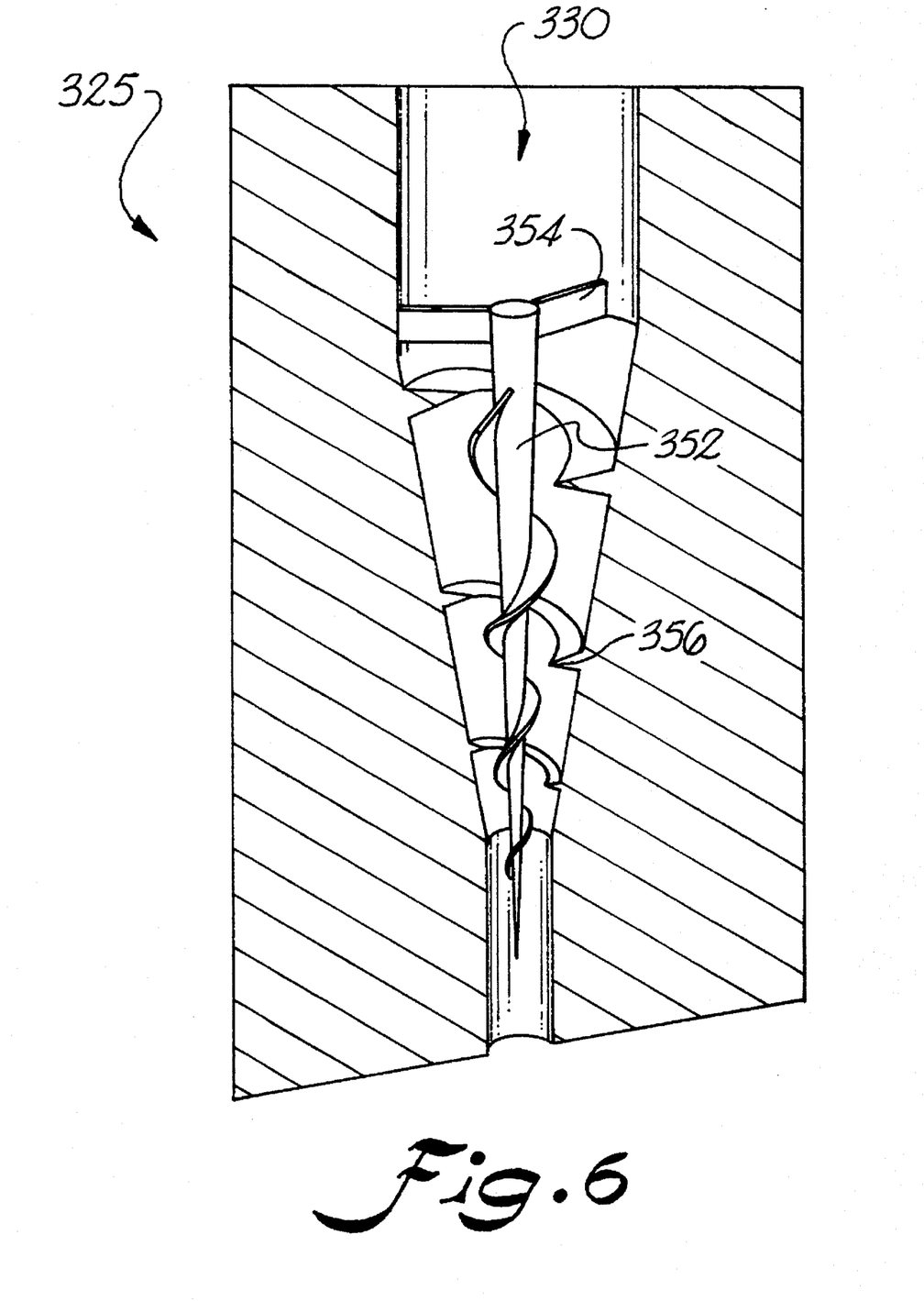
FIG. 6 is a perspective view of the mold illustrated in FIG. 5.

Besides molds for the linear orientation of polymeric substrates, the process of the present invention also encompasses molds for the rotational orientation of polymeric materials referred to as orthogonal unidirectional compressive orientational. Referring to FIGS. 5 and 6, one embodiment of a mold for rotationally orienting polymer chains within a polymer is illustrated. As shown, a mold generally 325 defines a mold cavity 330 which has a decreasing diameter. Positioned concentrically within mold cavity 330 is a threaded center portion 352. Center portion 352 is supported within cavity 330 by support arms 354 as shown in FIG. 6. Besides center portion 352 being threaded, mold cavity 330 also contains a thread 356 generally corresponding with the thread on center portion 352. The threads within the cavity are provided so as to cause the polymer to rotate as it is forced through the mold.

In this particular embodiment, the polymeric material must be heated prior to being forced through the mold cavity. Because the polymer is being rotated around center portion 352, a certain degree of fluidity is required. Referring to FIG. 5, a polymeric substrate 350 is shown being processed through mold 325. A compression bar 336 applies a force to polymer 350 as it is forced through the cavity. Similar to the process as described above, the polymeric material is being deformed in one direction. However, as polymer 350 moves through cavity 330, it moves in a spiral motion caused by contact with the threads. This action causes polymer chains within substrate 350 to assume a helical orientation. Upon exiting mold 225, the polymer is in the shape of a smaller diameter rod.

Preferably, mold 325 has a decreasing temperature profile as polymer 350 moves therethrough. In particular, preferably higher temperatures are maintained in the larger diameter areas of mold cavity 330. The temperature can be decreased in the smaller diameter areas for cooling the orthogonally oriented polymer.

The helical orientation of the polymer chains results in a polymer having increased strength and modulus not only in the longitudinal direction but also in the radial direction. Consequently, if the polymer is later formed into a bone screw, the threads of the screw will have increased strength. In other words, strength will be increased in the axial and radial directions.

Once a polymer material is deformed, oriented and cooled, the polymer can then be formed into a variety of useful articles as described above. The process of the present invention is particularly useful for forming bone fixation devices. Also, these devices are preferably made from bioabsorbable polymeric materials so that they would not have to be removed after being implanted. If made from bioabsorbable polymers, the bone fixation device should be made with sufficient strength to support loads normally supported by the fractured bone. Further, the bioabsorbable material should be able to retain the strength for a sufficient amount of time so as to allow proper healing of the bone. Using the process of the present invention, bone fixation devices made from bioabsorbable polymeric materials can be produced which have enhanced strength and modulus as not possible in prior art applications.

The amount of time required for the bone fixation device to retain its strength depends upon the particular application. Generally, the bone fixation device, if made from a bioabsorbable material, should retain its strength for a time period anywhere from 1 month to 2 years. In most applications, the polymer should retain at least 50% of its initial mechanical strength for at least one week after being implanted into the body. Preferably, the polymer should retain at least 50% of its strength for up to 3 months. It is believed that bone fixation devices made according to the process of the present invention can meet these and other standards depending upon particular bioabsorbable polymers chosen for use.

The present invention may be better understood with reference to the following examples.

EXAMPLE 1

Commercial ultra high molecular weight polyethylene (UHMW-PE) (GUR415), obtained from the Hoechst Celanese Corp. from Summitt, N.J., in powder form was compression molded into sheets at a temperature of 180° C. using a compression force of about 6 MPa (900 Psi) in a Carver Laboratory press (Model C). The sheets were cut into small pieces for solid state compression in a mold. Specifically, four samples were cut which had the following dimensions (length×width×thickness) before solid-state compression:

| Sample No. 1. | 21.5 × 17.5 × 6.7 mm |
| Sample No. 2. | 17.3 × 16.8 × 6.7 mm |
| Sample No. 3. | 17.6 × 17.2 × 6.7 mm |
| Sample No. 4. | 17.4 × 17.6 × 6.7 mm |

A mold similar to that illustrated in FIG. 2 was used. The samples were put in the center of the mold cavity causing the polymer to flow from two ends at high temperature under pressure. In particular, the mold containing a sample was put into a Carver Press and heated. When the temperature reached 125° C. (260° F.) a press load of 24,000 lb was applied The polymer was then cooled in the mold. The mold was taken out of the press when the temperature was below 40° C. (100° F.).

After solid-state compression, the samples had the following dimensions:

| Sample No. 1. | 72.2 × 17.7 × 2.02 mm |
| Sample No. 2. | 60.5 × 17.7 × 1.88 mm |
| Sample No. 3. | 65.4 × 17.7 × 1.78 mm |
| Sample No. 4. | 67.5 × 17.7 × 1.76 mm |

From the above samples, a dumbbell-shaped tensile test specimen was cut using a metal die. A tensile mechanical test was run on the specimens using a conventional Instron tensile testing machine. A load speed of 20 mm/min. and a gauge length of 20 mm were used. Table 1 lists the results. The solid-state compressed specimens showed no yielding point. The control refers to a sample that was not subjected to compression, deformation and orientation.

TABLE 1

Effects of Unidirectional Compression on Tensile Strength of UHMW-PE.

| Samples | Compression Ratio | Yield Stress (MPa) | Failure Stress (MPa) |
| --- | --- | --- | --- |
| No. 1 | 3.75 | 113.5 | 113.5 |
| No. 2 | 4.04 | 115.4 | 115.4 |
| No. 3 | 4.27 | 116.3 | 116.3 |
| No. 4 | 4.31 | 132.2 | 132.2 |
| Control | — | 25.2 | 54.0 |

EXAMPLE 2

A commercial polyetheretherketone (PEEK) marketed under the name VITREX from ICI Advanced Materials in Wilmington, Del. was used in this example. The PEEK was delivered in a form of an extruded bar. Samples were cut from this bar. Using the same procedures as in Example 1, the PEEK samples were unidirectionally compressed. The maximum temperature used to heat the samples was 305° C. (580° F.), while a press load of 30,000 lb was applied. Table 2 lists the results of the tensile mechanical tests.

TABLE 2

Effects of Unidirectional Compression on Tensile Strength of PEEK

| Samples | Compression Ratio | Yield Stress (MPa) |
| --- | --- | --- |
| PK1 | 1 | 250 |
| PK2 | 1 | 220 |
| Control | — | 105 |

EXAMPLE 3

Samples of bioabsorbable polymers were also processed according to the present invention in order to demonstrate tensile strength enhancement. Specifically, the bioabsorbable polymer tested was 10/90 Poly (D,L-Lactide-Co-L-Lactide) marketed under the name RESOMER LR909 by Boehringer Ingelheim.

Two sets of samples using the above polymer were prepared and tested. The first set of samples were made by compression molding the polymer between two plates, allowing the polymer to deform in all directions without achieving molecular chain orientation in any particular direction. A tensile test was performed on the samples as described in Example 1. The test conditions were as follows.

Machine parameters:

Sample rate (pts/sec): 9.103

Crosshead speed (mm/min): 20.0

Full scale load range (kg): 100.0

Gauge length (mm): 20.0

Grip distance (mm): 20.0

| Sample No. | Dimensions of samples: | |
| --- | --- | --- |
| | Width (mm) | Thickness (mm) |
| 1 | 4.95 | 1.355 |
| 2 | 4.95 | 1.385 |

-continued

Dimensions of samples:

| Sample No. | Width (mm) | Thickness (mm) |
|---|---|---|
| 3 | 4.95 | 1.370 |

The following tensile strength test results were obtained from the samples.

| Sample No. | Tensile Strength (Stress) (Kg/mm$^2$) | Load at Max. Load (Kg) | Displacement at Max. Load (mm) | Energy to Break Point (Kg-mm) | Load at z-slp Yield (Kg) |
|---|---|---|---|---|---|
| 1 | 6.993 | 46.91 | 1.867 | 46.03 | 46.91 |
| 2 | 5.599 | 38.39 | 1.465 | 27.82 | 38.39 |
| 3 | 7.507 | 50.91 | 2.197 | 56.97 | 50.91 |
| Mean: | 6.700 | 45.40 | 1.843 | 43.61 | 45.40 |

The second set of samples were made by unidirectionally deforming the polymeric material causing molecular chains within the material to orient in substantially one direction. The samples were deformed using a mold similar to the one illustrated in FIG. 3. The samples were pressed into films. A tensile strength test was performed on the samples under the same conditions and machine parameters as described above.

The dimensions of the samples were as follows:

| Sample No. | Width (mm) | Thickness (mm) |
|---|---|---|
| 1 | 4.95 | 1.835 |
| 2 | 4.95 | 1.835 |
| 3 | 4.95 | 1.835 |
| 4 | 4.95 | 1.835 |
| 5 | 4.95 | 1.440 |
| 6 | 4.95 | 1.500 |
| 7 | 4.95 | 1.670 |
| 8 | 4.95 | 1.670 |

From the above samples, the following results were obtained. The excluded samples slipped out of the grip of the machine and therefore represent failed tests.

| Sample No. | Tensile Strength (Stress) (Kg/mm$^2$) | Load at Max. Load (Kg) | Displacement at Max. Load (mm) | Energy to Break Point (Kg-mm) | Load at z-slp Yield (Kg) |
|---|---|---|---|---|---|
| Excluded | 5.951 | 54.06 | 13.040 | 1108.00 | 53.24 |
| Excluded | 5.722 | 51.98 | 2.783 | 368.30 | 51.98 |
| Excluded | 4.899 | 44.50 | 1.977 | 455.60 | 44.50 |
| 4 | 8.508 | 77.28 | 5.529 | 306.30 | 72.64 |
| 5 | 8.284 | 59.05 | 2.490 | 99.55 | 59.05 |
| 6 | 6.922 | 51.39 | 2.014 | 67.87 | 51.39 |
| 7 | 9.913 | 81.95 | 4.028 | 681.20 | 81.95 |
| Excluded | 10.250 | 84.71 | 3.772 | 490.90 | 84.71 |
| Excluded | 10.180 | 84.13 | 5.566 | 701.00 | 84.13 |
| Excluded | 9.140 | 75.56 | 4.833 | 587.50 | 75.56 |
| Mean: | 8.407 | 67.42 | 3.515 | 288.70 | 66.26 |

As shown from the above results, higher strengths were obtained when the polymeric substrates were oriented unidirectionally.

EXAMPLE 4

Approximately 60 grams of 10/90 poly(d,1-lactide-co-1-lactide) chip (RESOMER LR 909) was pressed at 20000 psi (9 metric tons) and 180° C. using a Carver Laboratory Press. The mold was cooled to room temperature under pressure. The resulting 10.75 cm×3.50 cm×1.14 cm polymer preform was allowed to anneal for 24 hours at 100° C. to encourage crystallite formation and growth. 1.80 cm wide strips were taken from the block and placed in an aluminum mold having a channel with a similar width and larger length. Specifically, a mold similar to the mold illustrated in FIG. 2 was used. Using a pressure of 20000 psi and a temperature of 130° C. (below the melting temperature), each preform was pressed to a desired thickness by varying the thickness of the overlying stainless steel bar which seated within the channel. Unidirectional, lengthwise flow was induced. Dimensions of length and thickness of the resulting polymeric plates were modified by approximately 34%. These were cut into square-ended bars 0.75×0.75×11.70 cm using a diamond bladed ban saw and then lathed to a rod with a diameter of 0.48 cm. The leading and trailing ends of the 4.5 cm long cylinders were tapped with size 8–32 and 10–40 threads, respectively, to produce an absorbable Herbert-type bone screw as shown in FIG. 1.

The bone screw that was formed was implanted into the distal portion of a goat femur which was removed from a goat cadaver. Specifically, the bone was cut into two portions. The screw was implanted into the bone in order to compress and secure the bone segments together. The bone screw exhibited sufficient strength to support the fractured bone.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to be limitative of the invention so further described in such appended claims.

What is claimed is:

1. A process for forming a bone fixation device from high strength polymeric materials, said process comprising the steps of:

providing a thermoplastic polymeric substrate having at least a 3% crystalline structure;

deforming said polymeric substrate under a compressive force in a mold cavity, said mold cavity having a width and a length, said width generally corresponding to the width of said polymeric substrate so that when said substrate is deformed, the substrate flows only in a lengthwise direction causing molecular chains contained within said substrate to orient unidirectionally for increasing the strength of said polymeric substrate; and subsequently forming said higher strength polymeric substrate into a bone fixation device.

2. The process as defined in claim 1, further comprising the step of heating said polymeric substrate prior to deforming said substrate to a temperature sufficient to soften the substrate without melting said crystalline structure.

3. The process as defined in claim 1, wherein said polymeric substrate is made from a bioabsorbable polymer.

4. The process as defined in claim 3, wherein said bioabsorbable polymer is a polymer selected from the group consisting of poly-alpha-hydroxy acids, polylactones, polyoxalates, and copolymers thereof.

5. The process as defined in claim 1, wherein said polymeric substrate has a crystalline structure of from about 5% to about 80%.

6. The process as defined in claim 5, wherein said polymeric substrate is deformed to an extent such that the thickness of said polymeric substrate is reduced by about 10% to about 85%.

7. The process as defined in claim 1, wherein said deforming step is repeated along a second predetermined direction different than said lengthwise direction prior to forming said bone fixation device.

8. A process for preparing polymeric materials for forming into bone fixation devices, said process comprising the steps of:

providing a thermoplastic polymer having an amorphous portion and a crystalline portion, said crystalline portion comprising at least about 3% of said polymer;

placing said thermoplastic polymer into a mold cavity, said mold cavity having a width and a length, said width generally corresponding to the width of said thermoplastic polymer;

heating said thermoplastic polymer to a temperature sufficient to soften said amorphous portion but at a temperature insufficient to melt said crystalline portion;

compressing said heated thermoplastic polymer while in said mold cavity at a pressure sufficient to deform said polymer in a lengthwise direction, thereby causing molecular chains within said polymer to orient for increasing the strength of said polymer; and cooling said compressed and oriented polymer for forming into a bone fixation device.

9. The process as defined in claim 8, wherein said crystalline portion is between about 20% and about 55% of said polymer.

10. The process as defined in claim 8, wherein said thermoplastic polymer is a bioabsorbable polymer.

11. The process as defined in claim 10, wherein said bioabsorbable polymer is a polymer selected from the group consisting of poly-alpha-hydroxy acids, polylactones, polyoxalates, and copolymers thereof.

12. The process as defined in claim 10, wherein said bioabsorbable polymer is a polymer selected from the group of consisting a polylactide, a polyglycolide, a poly-e-caprolactone, a polydioxanone, a poly-ortho-ester, a polyesteramide, a polyanhydride, and copolymers thereof.

13. The process as defined in claim 8, wherein said polymer is compressed with an inclined surface for also applying a shearing force to said polymer.

14. The process as defined in claim 8, wherein said polymer is compressed in a mold cavity having a gradually decreasing diameter, wherein said polymer is spirally forced through said cavity causing helical orientation of said molecular chains for increasing the longitudinal strength and the radial strength of said polymer.

15. The process as defined in claim 8, wherein the ratio of initial thickness to final thickness of said polymer after said compressing step is from about 1.2 to about 6.0.

16. The process as defined in claim 8, further comprising the step of machining said polymer into a bone fixation device.

17. A process for making bone fixation devices from bioabsorbable polymers with increased strength and modulus, said process comprising the steps of:

providing a bioabsorbable polymer having an amorphous portion and a crystalline portion, said crystalline portion comprising at least about 3% of said polymer;

heating said bioabsorbable polymer to a temperature between the softening point and the melting point of said polymer;

forcing said heated bioabsorbable polymer through a mold cavity, said mold cavity having a decreasing diameter and wherein said polymer is forced through said cavity in a spiral motion causing molecular chains contained within said polymer to extend in a helical orientation for increasing the longitudinal and radial strength of said polymer; and forming said polymer into a bone fixation device.

18. The process as defined in claim 17, wherein said bioabsorbable polymer is a polymer selected from the group consisting of a poly-alpha-hydroxy_acid, a polylactone, a polyoxalate and copolymers thereof.

19. The process as defined in claim 17, wherein said crystalline portion of said polymer is between about 5% and about 80%.

20. The process as defined in claim 17, further comprising the step of cooling said polymer while under compression after said polymer has been forced through said mold cavity.

* * * * *